(12) United States Patent
Fine

(10) Patent No.: US 9,063,152 B2
(45) Date of Patent: *Jun. 23, 2015

(54) METHOD FOR DETECTION OF ACTIVE PERIODONTAL DISEASE AT THE LOCAL TOOTH SITE

(75) Inventor: Daniel H. Fine, New York, NY (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 819 days.

This patent is subject to a terminal disclaimer.

(21) Appl. No.: 13/183,550

(22) Filed: Jul. 15, 2011

(65) Prior Publication Data

US 2012/0115135 A1 May 10, 2012

Related U.S. Application Data

(63) Continuation-in-part of application No. 12/724,272, filed on Mar. 15, 2010, now Pat. No. 8,389,015, which is a continuation-in-part of application No. PCT/US2008/076433, filed on Sep. 15, 2008.

(60) Provisional application No. 60/993,761, filed on Sep. 14, 2007, provisional application No. 61/364,687, filed on Jul. 15, 2010.

(51) Int. Cl.
G01N 33/68 (2006.01)

(52) U.S. Cl.
CPC ...... *G01N 33/6863* (2013.01); *G01N 2333/523* (2013.01); *G01N 2800/18* (2013.01)

(58) Field of Classification Search
CPC .................................................. G01N 33/6863
USPC ............................................................. 435/4
See application file for complete search history.

(56) References Cited

U.S. PATENT DOCUMENTS

2007/0003947 A1 1/2007 DeCarlo
2007/0054281 A1 3/2007 Liew et al.

OTHER PUBLICATIONS

Tew et al. "Relationship between gingival crevicular fluid and serum antibody titers in young adults with generalized and localized periodontitis", Infection and Immunity, 1985, 49(3):487-493.*
Reinhardt et al. "Gingival fluid IL-1 and IL-6 levels in refractory periodontitis", J Clin Periodontol, 1993, 20:225-231.*
Sudo et al. "Use of hydroxyapatite-coated glass beads for preclinical testing of potential antiplaque agnets", Applied and Environmental Microbiology, 1976, 32(3):428-432.*
Garlet, et al. "The Dual Role of p55 Tumor Necrosis Factor-A Receptor in *Actinobacillus actinomycetemcomitans*—Induced Experimental Periodontitis: Host Protection and Tissue Destruction." Clin. Exp. Immunol. 147(1): 128-138. (2005).
Emingil, et al. "Gingival Crevicular Fluid EMAP-II, MIP-1a and MIP-1b Levels of Patients with Periodontal Disease." J. Clin. Periodontol. 32: 880-885. (2005).
Rhodus, et al. "A Comparison of the Pro Inflammatory NF-nB-Dependent Cytokines: TNF-alpha, IL-1alpha, IL-6 and IL-8 in Different Oral Fluids from Oral Lichen Planus Patients." Clim. Immunol. 144: 278-283. (2005).
Miller, et al. "Current Developments in Salivary Diagnostics," Biomarkers in Medicine 4(1): 177-189. (2010).
Dental Radiography Definition: p. 1. (2011).
Killi, et al. "Collagenase-2 (MMP-8) and collagenase-3 (MMP-13) in adult periodontits: molecular forms and levels in gingival crevicular fluid and immunolocalisation in gingival tissue." J. Clin. Periodontol. 29: 224-232. (2002).
Fairney, et al. "Studies on the measurement of 25-hydroxy vitamin D in human saliva." British J. of Nutrition 57: 13-25. (1989).

* cited by examiner

*Primary Examiner* — Bin Shen
(74) *Attorney, Agent, or Firm* — Fox Rothschild LLP

(57) ABSTRACT

A method for site-specific detection and early diagnosis of periodontal disease using periodontal pocket fluid biomarkers is disclosed.

8 Claims, 2 Drawing Sheets

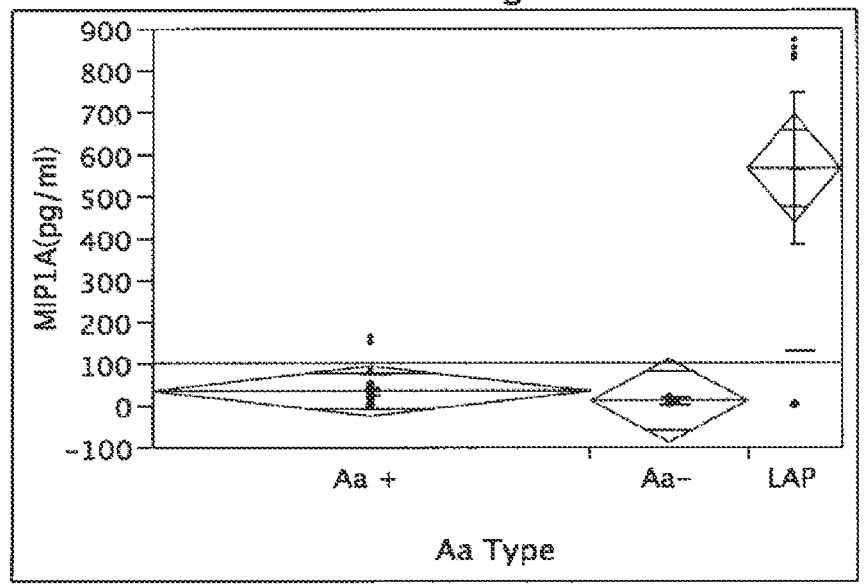
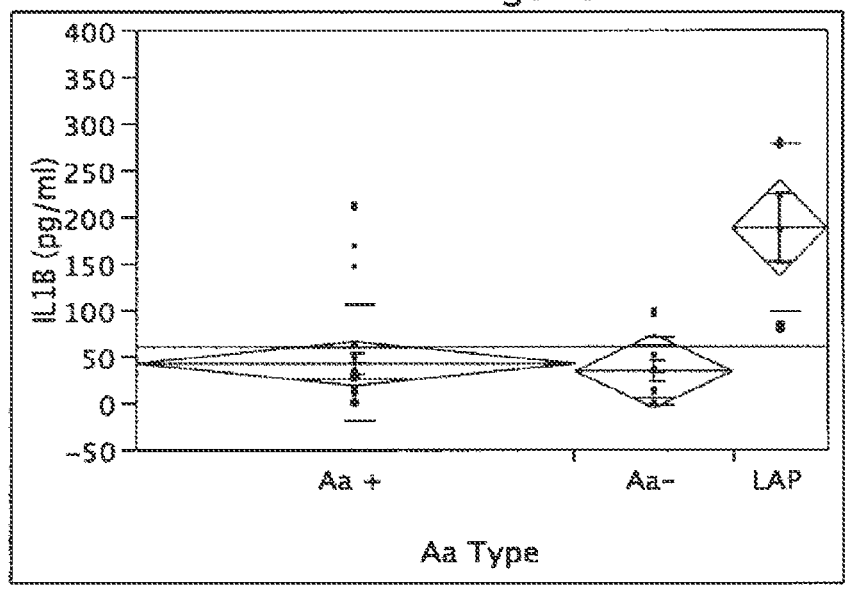

METHOD FOR DETECTION OF ACTIVE PERIODONTAL DISEASE AT THE LOCAL TOOTH SITE

CROSS-REFERENCE TO RELATED APPLICATIONS

This application is a continuation-in-part of U.S. application Ser. No. 12/724,272, filed Mar. 15, 2010, which is a continuation-in-part of International Patent Application No. PCT/US2008/076433, filed Sep. 15, 2008, which claims priority to U.S. Provisional Application No. 60/993,761, filed Sep. 14, 2007. This application also claims the benefit of U.S. Provisional Application No. 61/364,687, filed Jul. 15, 2010. All of the foregoing applications are hereby incorporated by reference in their entireties.

STATEMENT REGARDING FEDERALLY FUNDED RESEARCH

This invention was made with government support under Grant RO1 DE-017968 awarded by the National Institute of Health. Accordingly, the U.S. Government has certain rights in this invention.

FIELD OF THE INVENTION

The present invention relates to the detection and diagnosis of periodontal disease prior to the occurrence of bone loss.

BACKGROUND OF THE INVENTION

Periodontal disease is an inflammatory disease that begins as an inflammation of the gingival soft tissues (gums) and then proceeds to affect the supporting structures of the tooth in its bony socket. At present, periodontal disease is the most pressing dental malady that if untreated can result in tooth loss. Further, recent evidence suggests that this chronic dental infection, and its resulting widespread oral inflammation, can contribute to an increased risk for systemic complications including an increased risk for heart disease. With the discovery of fluoride and the resulting reduction in the prevalence of caries, periodontal disease and its earliest manifestation, gingivitis, has become the most prevalent and costly of dental infections. Gingivitis and its sequelae, periodontal disease, affects over 50% of the adult population.

Oral bacteria form a plaque biofilm that can initiate gingival inflammation. Under the appropriate circumstances, gingivitis can lead to periodontitis, which is manifested as an inflammatory-induced destruction of the bony support of the teeth. The disease is pandemic, costly, can result in tooth loss, and is also conjectured to increase the risk for coronary heart disease and other systemic conditions.

Currently, the existing technology used by a dentist or dental health professional to detect periodontal disease relies on a clinical examination that includes a periodontal probe and/or an x-ray. It is well known that these methods are imperfect because they are operator sensitive, time consuming and detect only past history of tissue destruction. Thus, there remains a need for improved ways of detecting periodontal disease.

Bone loss, the ultimate proof of disease, is measured by radiograph and is an end stage of disease, which for the most part is irreversible. The periodontal complex is best described as a peg in a socket: the tooth represented by the peg, and the alveolus, or surrounding bone, represented by the socket. The tooth is connected to its socket by collagen fibers that enable the tooth to respond to the forces of mastication and clenching and grinding. Inflammation causes bone loss that occurs by virtue of osteoclasts that eat away the bone and widen the socket, leading the affected tooth to become loose and ultimately non-functional. Bone loss of the periodontal tissues takes anywhere from 6-18 months to manifest itself.

Diagnosis of periodontal disease is initially based on measurements of soft tissue detachment from the tooth, which results in a periodontal pocket. Methods used to probe for attachment loss and to detect bone loss, the hallmark of the irreversible stage of periodontal disease, while quite specific are not very sensitive, and often delay diagnosis. A number of scientific advances have spawned technologies that are capable of detecting nanograms or picograms levels of inflammatory biomarkers in bodily fluids. These technologies could potentially be used to develop tests for early clinical diagnosis, which, if successful, could provide earlier warning of disease onset as compared to the relatively insensitive methods used currently.

SUMMARY OF THE INVENTION

The present invention is directed in part to a method to determine the location of periodontal disease within a patient's mouth comprising obtaining samples of fluid from periodontal pocket sites and analyzing the fluid samples individually to identify the presence of a biomarker at a level that indicates periodontal disease. In one embodiment of the invention, the biomarker is either Macrophage Inflammatory Protein 1 alpha (MIP-1$\alpha$) or Interleukin-1 beta (IL-1$\beta$).

In one embodiment of the invention, the step of obtaining samples of fluid comprises individually depositing selected adsorptive articles into respective periodontal pocket sites, allowing a selected period of time for adsorption of fluid within the periodontal pocket sites by the adsorptive articles, individually retrieving the adsorptive articles from the respective periodontal pocket sites and placing the adsorptive articles into respective test containers corresponding to the respective periodontal pocket sites. In certain embodiments, the selected adsorptive articles are beads of hydroxyapatite.

In one embodiment of the invention, the level of the biomarker is greater than about 200 pg/ml. In other embodiments, the level is from about 200 pg/ml to 2000 pg/ml, or from about 500 pg/ml to about 1,500 pg/ml, or from about 750 pg/ml to about 1250 pg/ml.

In one embodiment of the invention, the biomarker is identified prior to radiographic evidence of bone loss.

Another aspect of the present invention is directed to a kit for detecting the location of periodontal disease within a patient's mouth comprising a reagent that indicates the presence of a biomarker in fluid located in a periodontal pocket site at a level that indicates periodontal disease at the site and a device for contacting the fluid with the biomarker. In one embodiment of this aspect of the invention, the kit includes instructions that explain that the presence of the biomarker at the level indicates early-stage periodontal disease at the site. In one embodiment, the biomarker used in this kit is either MIP-1$\alpha$ or IL-1$\beta$. In a certain embodiment, the reagent is a fluorophore.

In certain embodiments of this aspect of the invention, the level of the biomarker is greater than about 200 pg/ml. In other embodiments, the level is from about 200 pg/ml to 2000 pg/ml, or from about 500 pg/ml to about 1,500 pg/ml, or from about 750 pg/ml to about 1250 pg/ml.

BRIEF DESCRIPTION OF THE DRAWINGS

FIG. 1A is a graphical depiction of the measured level of MIP-1$\alpha$ as compared to the *Aggregatibacter actinomycetemcomitans* (Aa) type.

FIG. 1B is a graphical depiction of the measured level of IL-1β as compared to the Aa type.

DETAILED DESCRIPTION OF THE INVENTION

Figure 2A:
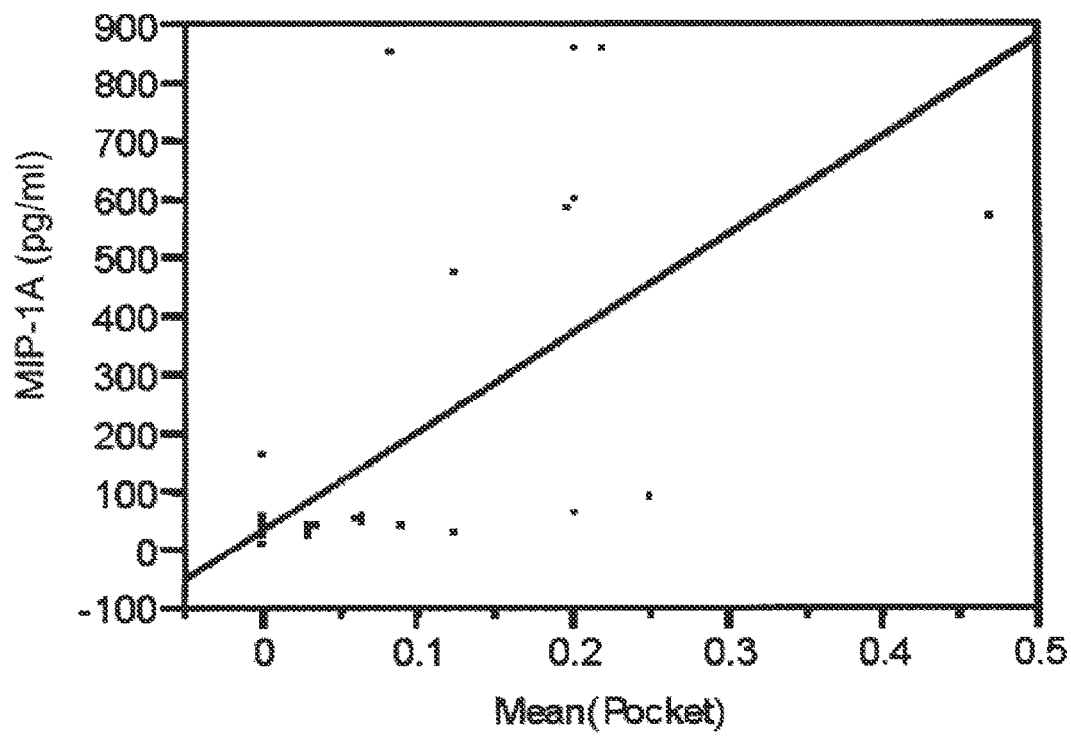
FIG. 2A is a graphical depiction of the relationship between increasing mean pocket depths and increasing levels of MIP-1α.

One embodiment of the present invention relates to the detection of an elevated presence of a biomarker in a fluid sample of a patient that would indicate periodontal disease. Preferably, the biomarker is a cytokine and more preferably the cytokine is MIP-1α, a chemokine that initiates conversion of pleuripotential cells to differentiate into osteoclasts. MIP-1α can be detected in patients prior to bone loss and thus acts as an early indicator of the onset of periodontal disease. Certain embodiments of this invention allow a practitioner, or a patient using a home test, to use a fluid sample found in the patient's mouth, e.g., saliva, to assess the earliest stages of periodontal bone loss so that a vulnerable patient can be identified. This test allows a patient to seek early treatment that can prevent further loss and thus save his or her teeth. Further, in another embodiment of the invention, once the patient has been identified, the dentist can pinpoint the tooth or teeth in the patient's mouth that require treatment so that treatment could be limited to those teeth in the patient's mouth that require intervention.

In certain embodiments directed to the presence of MIP-1α in bodily fluid, the level that is used as an indicator of to indicate early-stage periodontal bone loss can be, e.g., greater than about 200 pg/ml, greater than about 400 pg/ml, greater than about 600 pg/ml, or greater than about 800 pg/ml.

In other embodiments, the presence of MIP-1α in bodily fluid is detected at a level from about 200 pg/ml to about 2000 pg/ml, from about 500 pg/ml to about 1,500 pg/ml, or from about 750 pg/ml to about 1,250 pg/ml to indicate early-stage periodontal bone loss.

In other embodiments, the biomarker is identified prior to radiographic evidence of bone loss. This allows early intervention to prevent or minimize progression of the disease and also prevents or minimizes the exposure of the patient to radiation.

The present invention also is directed to a kit for detecting early-stage periodontal bone loss comprising a reagent that indicates the presence of a biomarker in a bodily fluid of a patient at a level that indicates early-stage periodontal bone loss and a device for contacting the bodily fluid with the biomarker.

The kit optionally includes instructions that explain that the presence of the biomarker at the specified level indicates early-stage periodontal bone loss.

In certain embodiments, the invention includes an apparatus for mixing the reagent with the bodily fluid. In another embodiment, the reagent can be on a strip that is contacted with saliva by placing the strip on the tongue of the patient.

In another embodiment of the present invention, a method is provided for detecting the affected tooth or teeth of a patient who may have periodontal disease. This method provides for clinical chair-side measure of tissue destruction that has already taken place in the oral cavity of a patient and tests for the early diagnosis of periodontal disease. This embodiment is designed to allow a dentist or dental health professional to collect samples from the region below the gum at each tooth site in the mouth. In a dental office visit, a dentist typically uses a periodontal probe that has markings and measures the depth of pockets to determine any signs of periodontal disease. The probe is inserted in the periodontal pocket between the tooth and gum and millimeter measures are recorded. Each tooth has both a mesial and distal periodontal pocket from which a fluid sample may be extracted from the patient. In this embodiment of the invention, fluid is extracted from the local periodontal pocket site which can be used to assess biological markers that precede tissue destruction.

The fluid sample may be obtained by any method known in the art, including, but not limited to, sterile endodontic paper points, micropipettes, capillary tubes, and hydroxyapatite beads. When endodontic paper points are used, an absorbent paper point is inserted into each pocket for about 20 seconds. The absorbed material can then be eluted to test it in the Luminex xMap system described below.

The fluid sample captured from the local site is taken from the mouth and used in a biological assay that is performed chair-side. The assay performs an evaluation of the level of MIP-1α and other biomarkers of bone loss, which will indicate whether the local site is undergoing destruction due to periodontal disease. By analyzing each periodontal pocket fluid sample individually, the practitioner is able to identify which tooth is experiencing tissue destruction due to periodontal disease.

The different embodiments of the present invention may be used in conjunction with each other. For example, the embodiment described above that performs an assay on a salivary sample will only indicate if a particular patient is undergoing bone loss. In other words, this assay can only identify disease at the patient level but cannot indicate the specific site in the patient's mouth that is vulnerable. Because there are 28 teeth in a patient's mouth, any one of them could be undergoing tissue destruction and, resultantly, be the source of the biomarker. Accordingly, a practitioner may use another embodiment of this invention to test the individual periodontal pocket sites.

In certain embodiments of the present invention, the practitioner can probe each periodontal pocket site and then insert an adsorptive article, such as a small hydroxyapatite bead, into the pocket. While remaining in the site for a selected period of time, the adsorptive article will adsorb the fluid in the pocket. The practitioner then retrieves the article from the periodontal pocket and places the article into respective test containers corresponding to the respective periodontal pocket sites. The fluid is then eluted from the article and then will be diluted in a solution contained in the tube. The solution in the tube will have antibody to MIP-1α or other bone resorptive proteins. After elution from the article, a secondary reagent will be added that will cause a colorimetric change to develop that will show the presence of levels of MIP-1α that indicate bone loss caused by periodontal disease at the site. This will enable the dentist to identify the active site that is undergoing active bone loss. The success of the treatment can be monitored through repeated testing.

In a particular embodiment, the method or kit utilizes Luminex xMAP technology to detect the biomarker. In one embodiment, a fluid sample is placed into plate prepared with internally labeled fluorophore beads. The mixture of sample and beads is agitated and incubated. Labeled dyes contained within the beads are excited, exposed to a washing strategy, and then subjected to detection of activated fluorophores.

In certain embodiments, the biomarkers used to detect early-stage periodontal bone loss include, but are not limited to, Osteocalcin, RANK L and soluble RANKL, Osteoprotegrin, MIP-1α and Alkaline phosphatase.

Other embodiments of the invention are directed to a method of detecting increased periodontal pocket depth in a patient comprising identifying a biomarker in a bodily fluid of a patient wherein the level of the biomarker directly correlates with the pocket depth, and corresponding kits.

In other embodiments of the present invention, a dental practitioner can titrate pressure being exerted on teeth so that pressure to move teeth can be increased or decreased to allow for more or less bone resorption (titrate pressure vs. movement) and corresponding tooth movement that accompanies this pressure.

Other embodiments of the invention are directed to a method of detecting increased periodontal pocket depth in a patient comprising identifying a biomarker in a bodily fluid of a patient wherein the level of the biomarker directly correlates with the pocket depth, and corresponding kits.

EXAMPLES

Example 1

This study details the survey of cytokines/chemokines obtained from saliva of at risk subjects who were enrolled in a longitudinal cohort study of a specialized form of periodontal disease that occurs in adolescents, localized aggressive periodontitis (LAP).

The study involves the association of *Aggregatibacter actinomycetemcomitans* (Aa) with the initiation of LAP. This disease has afforded us the opportunity to study bone loss because, 1) the disease occurs in juveniles (this is a rare event and thus makes the disease easier to identify when it happens because it is so rare in children), 2) the disease is localized to first molars and therefore we can focus on first molars (there are four; as opposed to the 28 other teeth which we would have to follow if we studied adults), 3) it is rapidly progressive (and occurs in one to three years as opposed to disease in adults which has no well defined time limit) and 4) is associated with a particular microbe (Aa; as opposed to adult periodontal disease, which has an ill defined provoking microflora).

Saliva from subjects who were healthy and *A. actinomycetemcomitans* positive at screening and who developed bone loss, were compared to subjects who were *A. actinomycetemcomitans*-positive and *A. actinomycetemcomitans*-negative who remained healthy. The goal of this study was to determine whether salivary biomarkers that were indicative of the initial stages of inflammatory periodontitis and bone loss, could be detected prior to radiographic evidence of bone loss in a group of LAP susceptible subjects. This example documents the elevation of MIP1α, a chemokine that recruits osteoclast progenitors, in the saliva of students who developed bone loss. Results from the example indicate that MIP-1α serves as a biomarker of early events in inflammatory induced periodontal bone loss that precedes radiographic evidence.

Materials and Methods

A calibration exercise was conducted for measurement of periodontal pocketing, attachment loss and radiographic detection of bone loss. Results of the calibration exercise demonstrated 80% inter-examiner agreement and 90% intra-examiner repeatability. A detailed description of the procedures has been reported in Fine D. H., et al. *Aggregatibacter actinomycetemcomitans* and its relationship to initiation of localized aggressive periodontitis: Longitudinal cohort study of initially healthy adolescents. *J. Clin. Microbiol.* 2007; 45:3859-3869.

At the screening visit, each student was sampled and examined for oral soft tissue lesions, caries and periodontal disease. For the periodontal examination, standard probing measurements were done on six surfaces on each tooth. Any site≥4 mm was re-examined for attachment level measurements. Potential disease was defined as any pocket≥6 mm with associated attachment loss≥2 mm. Students in this category were scheduled for recall within a 3-month period or sooner in order to minimize any irreversible consequences of disease. Each student was given a prophylaxis and oral hygiene instruction.

A recall visit was scheduled within six months of screening or sooner depending on the students' periodontal status. Recall was identical to screening except for the addition of 2-4 horizontal bitewing radiographs for detection of bone loss.

Most participants were students with a mixed dentition and partially erupted molar teeth which adds to measurement variability. As a result of this potential source of measurement error, we chose to use radiographs as the main determinant of periodontal disease. Disease was defined as crestal loss of lamina dura and interproximal alveolar bone resorption in the region of one or more molars or incisors as visualized by radiography. Pocket depths and attachment levels were also recorded but in the initial analysis evidence of bone loss was required since our goal was to relate the presence of specific cytokines to bone loss. As mentioned, to prevent any serious consequences relating to the aggressive loss of bone, subjects with potential disease were re-scheduled for re-probing and attachment level measurements as well as radiographic evaluation within a 3-month period following screening. On evidence of bone loss the student was referred for treatment provided at no cost in the University practice facility. If radiographs did not show bone loss, students were returned to the 6-month recall schedule.

In periodontal disease the markers come from the pocket overlying the infected tooth and then these proteins spill over into saliva. We have done a pilot study in which we studied the presence of RANKL in saliva and compared it to that seen in crevicular fluid in pockets surrounding teeth that were either healthy or periodontally diseased. We measured these elements in gingival crevicular fluid in healthy sites in some patients and in pockets in diseased patients and found the presence of these markers in saliva at a detectable level even in cases where only one pocket existed. These results indicate that saliva is capable of detecting these elements from just one pocket site.

At each visit, the following samples were collected: unstimulated saliva, buccal epithelial cells (BEC), and subgingival plaque from pockets≥5 mm. Saliva was used to assess inflammatory cytokines. BEC and subgingival plaque samples were used to determine the presence or absence of *A. actinomycetemcomitans*. For saliva collection, students expectorated into a 50 ml wide-mouthed polystyrene tube placed over ice. Five ml of saliva was collected and then subjected to centrifugation at 10,000×g for 30 min. The supernatant was decanted and the clarified saliva was stored at −80° C. BEC samples were obtained by gently scraping the surface of the buccal mucosa with a wooden tongue depressor. Cells were collected in a 50 ml Pyrex tube containing 2 ml of phosphate buffered saline (PBS). BECs were subjected to vortex agitation for 15 seconds after which 100 ul was removed for plating on AAGM agar. The remaining reservoir of epithelial cells was stored at −80° C. Pocket samples were taken for any subgingival pocket>5 mm by placing two sterile endodontic paper points in the pocket site for 10 sec. All sites sampled in a given subject were pooled in 2 ml of PBS, subjected to vortex agitation for 15 sec, after which 100 ul was removed for plating on AAGM agar for isolation of *A. actinomycetemcomitans*.

One thousand and forty-five students ages 11-17 were screened for periodontal disease and sampled for *A. actinomycetemcomitans*. 147 of these students were shown to harbor *A. actinomycetemcomitans* (Aa-positive). A longitudinal study was designed to follow Aa-positive and matched Aa-negative students at 6-month intervals for 2-3 years. 37 Aa-positive and 58 Aa-negative students have been followed for ≥1 yr and seven of these 36 who were healthy at screening have developed bone loss. One of the 37 students had bone loss at screening, while none of the 58 Aa-negative students have shown bone loss at any visit. Initially, cytokines were assessed in the saliva of 7 Aa-positive students who developed bone loss 6-12 mo prior to bone loss. These samples were compared to samples obtained from 7 Aa-positive and 7 Aa-negative students who remained healthy and were matched for sex, age and race to the 7 students who developed bone loss. Following evaluation of these 21 students, 13 Aa-negative and 13 Aa-positive students were added for analysis as was one Aa-positive student who had bone loss at screening. This study reports on cytokine levels from the stored saliva obtained from these 48 students.

Microbiological and Cytokine Procedures

For identification of *A. actinomycetemcomitans*-positive students, 100 ul aliquots of BECs and/or pocket samples were plated on AAGM agar and grown for 3-4 days in an incubator at 37° C. in 10% $CO_2$. *A. actinomycetemcomitans* was identified by biochemical testing and by the polymerase chain reaction (PCR).

*A. actinomycetemcomitans*-negative students were identified as follows. Stored BEC and/or pockets samples were subjected to DNA extraction and evaluation of *A. actinomycetemcomitans* DNA by PCR. DNA was extracted using the Qiagen DNeasy Kit [Qiagen Inc., Valencia, Calif., Cat #69504] Gram-Negative Bacteria Protocol. This procedure was repeated 2×'s to confirm that the student was *A. actinomycetemcomitans*-negative.

The presence and level of 21 cytokines in saliva was determined by the Luminex xMAP technology. 100 ul salivary sample was placed into a 96-well plate prepared with internally labeled fluorophore beads. The mixture of sample and beads was agitated and incubated for 2 hrs at RT. Labeled dyes contained within the beads were excited by laser, exposed to a washing strategy, and then subjected to detection of activated fluorophores. All tests are run simultaneously to assure standardization. The limit of detection was between 1-500 pg.

Statistical Analysis

The three groups (*A. actinomycetemcomitans*-positive with bone loss, *A. actinomycetemcomitans*-positive healthy and *A. actinomycetemcomitans*-negative healthy) were compared. The statistical difference between groups for each of the 21 cytokine/chemokine was analyzed by ANOVA. Differences were considered significant if they achieved a p value of ≤0.05.

Similar statistical comparisons were made for *A. actinomycetemcomitans*-positive students to determine whether recovery from buccal sites differed from pocket sites. Tukey's Honest Statistical Difference (HSD) test was performed to elucidate the relationship between pairs of comparison within the ANOVA.

In addition, a bivariate linear regression analysis was used to evaluate cytokine levels vs. pocket depth or maximum number of pockets per individual. Due to the distribution of the data, Spearman's rank order correlations were used to describe the relationship between the two cytokines and mean pocket depth. The strength of the cytokines and *A. actinomycetemcomitans* to predict future pocket depth were also compared with ANCOVA (adjusting for age, gender and race). This was done in order to determine which variable was a better candidate for predicting future periodontal destruction as evidenced by the number of 6 mm. pockets. IL-1β and MIP-1α sensitivity and specificity relative to detection of bone loss were determined. Sensitivity was defined as the number of bone loss positive students that were above threshold levels (for MIP-1α or IL-1β) divided by the total number of bone loss positive students. Specificity was defined as the number of bone loss negative students below threshold levels (for MIP-1α or IL-1β) divided by the total number of bone loss negative students.

Results

Table 1 shows the demographic distribution of students evaluated; 26 were female, 20 were African-American and 18 were Hispanic.

TABLE 1

Demographics of Subjects

| Subject Category | Aa-Negative Healthy | Aa-Positive Healthy | Aa-Positive LAP |
|---|---|---|---|
| N | 20 | 20 | 8 |
| Mean Age | 15.1 ± 1.2 | 15.3 ± 1.4 | 15.8 ± 1.0 |
| Males | 8 | 10 | 4 |
| Females | 12 | 10 | 4 |
| African-American | 8 | 10 | 5 |
| Hispanics | 10 | 8 | 3 |
| Caucasian | 1 | 1 | 0 |
| Asian | 1 | 1 | 0 |

Aa = *A. actinomycetemcomitans*

The students' ages were approximately similar. The initial evaluation of IL-1β and MIP-1α compared 7 students in each of 3 groups as indicated in Table 2.

TABLE 2

Relationship of Cytokine Levels in Saliva to Disease Levels

| | Aa-Negative Healthy (N = 7) | Aa-Positive Healthy (N = 7) | Aa-Positive LAP (N = 7) |
|---|---|---|---|
| IL-1β | 21.6 ± 19.1 | 13.5 ± 4.3 | 39.2 ± 26.2 |
| MIP-1α | 20.5 ± 6.8 | 28.8 ± 6.8 | 420 ± 42.8* |

Aa—*A. actinomycetemcomitans*

*= Significantly higher by ANOVA and post-hoc analyses Cytokine/chemokine level reported as pg/ml The following cytokines: IL-2, IL-3, IL-4, IL-5, IL-9, RANTES, VEGF, KC, and TNFα, were not detected. The following cytokines: GMCSF, IFN.gamma., IL-1α, IL-6, IL-8, IL-10, IL-12 (p40), 1L-12 (p70), IL-13, IL-17, were detected but no significant differences were found when the three groups were compared. IL-1β was elevated in the *A. actinomycetemcomitans*-positive breakdown group as compared to the two other groups but differences were not significant (p=0.147; Table 2). However, MIP-1α (pg/ml) was significantly elevated in the *A. actinomycetemcomitans*-positive LAP group 6-9 months prior to detection of bone loss (p≤0.001; Table 2). While 7 of 7 *A. actinomycetemcomitans*-positive students showed elevated levels of MIP-1α prior to bone loss, only one of the 14 control students showed elevated MIP-1α and the level was half that seen in the students with bone loss.

In an effort to confirm this data, we added students in the *A. actinomycetemcomitans*-positive and *A. actinomycetemcomitans*-negative groups who remained healthy to determine if any of these students exceeded the basal levels of MIP-1α or IL-1β seen in the initial analysis. Only one additional student could be added to the bone loss group since only eight students in total showed bone loss. This one student had bone loss at screening. The levels of MIP-1α remained approximately 50 times higher in the group that experienced bone loss as compared to controls ($p \leq 0.0001$; FIG. 1a). When additional healthy students were included, the levels of IL-1β were statistically significantly elevated in the bone loss group as compared to controls (FIG. 1b).

MIP-1α had a specificity of 96.8% (30=number of bone loss negatives below threshold levels of 100 pg/ml/30+1=total number of bone loss negatives) and a sensitivity of 100% (7=number of bone loss positive above the threshold/7 total number of students with bone loss), while IL-1β had a specificity of 90.3% ($28/31$) and a sensitivity of 85.7% ($6/7$) for bone loss.

Figure 2B:
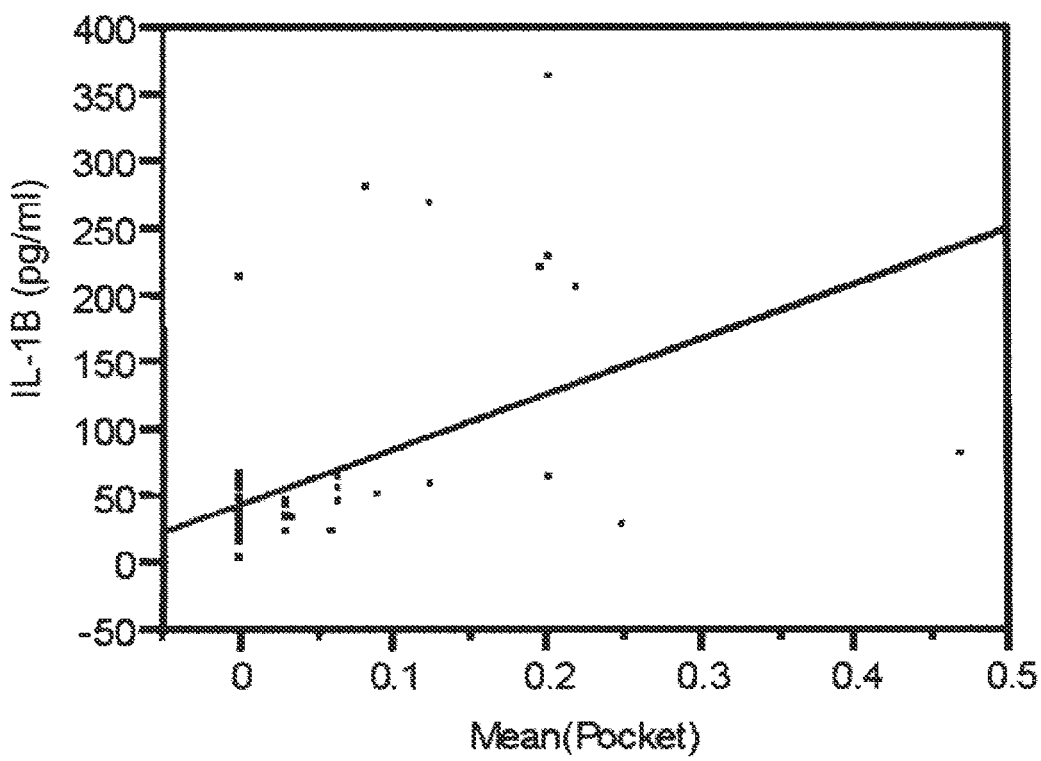
FIG. 2B is a graphical depiction of the relationship between increasing mean pocket depths and increasing levels of IL-1β.

Because only those students with *A. actinomycetemcomitans* developed bone loss, we compared sites of recovery of *A. actinomycetemcomitans* to levels of MIP-1α and IL-1β in these *A. actinomycetemcomitans*-positive students using a Student's t-test. No differences were found when cytokine levels in saliva were assessed in students where *A. actinomycetemcomitans* was recovered from buccal sites as compared to *A. actinomycetemcomitans* recovered from pocket sites (data not shown). However when pocket depths were evaluated and compared to cytokine levels by linear regression analysis, a direct relationship between increasing mean pocket depths and increasing levels of MIP-1α ($r=0.57$; $p<0.0001$) and IL-1β ($r=0.56$; $p<0.0001$) was seen (FIGS. 2a, 2b).

Table 3 presents the results of ANCOVA in which the independent variables in the table (time in study, age, gender, race, presence of *A. actinomycetemcomitans*, IL-1β (pg/ml), and MIP-1α (pg/ml) were related to the number of six mm pockets, the dependent variable.

TABLE 3

Analysis of Covariance of all factors as they relate to the number of 6 mm pockets

| Variable | DF | Sum of Squares | Prob > F |
|---|---|---|---|
| Time from sample | 1 | 0.12 | 0.778 |
| Age | 1 | 1.65 | 0.292 |
| Gender | 1 | 0.59 | 0.525 |
| Race | 5 | 0.84 | 0.988 |
| Aa | 1 | 2.39 | 0.206 |
| IL-1β (pg/ml) | 1 | 5.14 | 0.067 |
| MIP-1α (pg/ml) | 1 | 17.59 | 0.001 |

The goal of the analysis was to determine which of three variables (*A. actinomycetemcomitans*, MIP-1α (pg/ml), and IL-1β (pg/ml) had the strongest relationship with periodontal destruction as measured by the number of six mm. pockets. The sums of squares and the significance levels indicate that the strongest relationship was between MIP-1α (pg/ml) and the sum of 6 mm. pockets (ss. 17.59, p<0.001). It should be noted that if IL-1β (pg/ml), or *A. actinomycetemcomitans* were the only variable in the model in addition to the demographic covariates, that they were also significantly related to the sum of the six mm pockets (analysis not shown). Thus, *A. actinomycetemcomitans* and IL-1β parallel the elevations seen in MIP-1α. This suggests that the variables are co-linear and that MIP-1α (pg/ml) had the strongest relationship with periodontal destruction as measured by the number of six mm pockets of the three variables assessed (see Table 3).

Discussion

It is proposed that periodontal disease progresses from increased pocket depth to bone loss which marks the decisive and irreversible stage of disease. Cross-sectional studies are limited in their ability to capture time dependent events that would herald the transition from pocket deepening to attachment loss to bone loss. In contrast, longitudinal studies are capable of highlighting these critically important sequential events. Radiographs lack the sensitivity required to define the transition from attachment loss to early bone loss and thus can only depict past history of disease. Radiographic depiction of bone loss relies on detection of a threshold of calcium depletion in bone, which can begin 6-9 months before this event can be visualized. This delayed discovery postpones and complicates treatment. Therefore, a biomarker that predates x-ray evidence of bone loss by several months is highly desirable.

Recently, our group performed a longitudinal study in Newark to focus on African-American and Hispanic children who harbored *A. actinomycetemcomitans* and thus were thought to be at risk for LAP. Results indicated that LAP prevalence in African-American and Hispanic children from Newark was similar to data seen in the NHANES study. We were particularly interested in the risk projected for healthy children who harbored *A. actinomycetemcomitans*. Thus a longitudinal study was designed to follow initially healthy *A. actinomycetemcomitans* positive and *A. actinomycetemcomitans*-negative students at 6-9 month intervals. 38 *A. actinomycetemcomitans*-positive healthy children were followed for ≥1 yr and about 18% (7 of 37) developed bone loss while none of the 58 matched *A. actinomycetemcomitans-negative* students developed bone loss. Of all the students followed, 1.8% (7 of the 96) developed LAP, which approximates the LAP national average for African-American and Hispanic children. 30 of 37 who harbored *A. actinomycetemcomitans* (about 80%) did not show bone loss and remained healthy over the course of the study. A second longitudinal study done in Morocco also indicated that children with *A. actinomycetemcomitans* were at a significant increased risk for LAP. A test discriminating between those *A. actinomycetemcomitans*-positive subjects who develop disease (18%), those *A. actinomycetemcomitans*-positive subjects who may develop disease from those who will remain healthy is warranted.

The data derived from this study is based on a subset of students who over time went from health to bone loss. Bone loss was used to identify disease because it marked a well-defined step in the disease process that is irreversible and can be separated from inflammatory gingivitis, which is reversible. Thus, conclusions derived from this study are based on a strict definition of periodontal disease that separate groups by one event, namely, bone loss. Students with bone loss showed a 50-fold elevation of MIP1α, a chemokine that stimulates recruitment of osteoclast progenitors and the formation of osteoclasts. Chemokines are small (8-12 kDa) biologically active proteins, secreted by inflammatory cells. The chemokines form a gradient that attracts specific cells. The result is an advancing front of highly active cells that confront the challenging irritants. MIP-1α is a biologically active chemokine primarily known as a chemotactic agent for monocytes. However, MIP-1α also acts to stimulate monocytes and/or osteoclast progenitor cells to become active osteoclasts. In the pathogenesis of multiple myeloma, MIP-1α has been shown to be elevated several months prior to radiographic detection of bone loss. With respect to dental infections, MIP-1α has been shown to be elevated in patients with periapical osseous lesions, and in periodontal disease.

Our secondary analysis showed that IL-1β was also elevated. Several in vivo studies have shown that IL-1β levels in gingival crevice fluid are elevated in sites that show alveolar bone loss in patients with active periodontal disease. Most recently it was shown that *A. actinomycetemcomitans* and *Porphyromonas gingivalis* LPS induced MIP-1α expression in PMNs and gingival epithelial cells. Further, it was shown that *A. actinomycetemcomitans* and *P. gingivalis* LPS and IL-1β can stimulate these progenitor cells to activate osteoclasts.

The findings from the current study were considered highly informative for the following reasons. Of 21 cytokines assessed, only one, MIP-1α, was significantly elevated in the saliva in our initial assay. The fact that MIP-1α has been shown to have a powerful biological link to bone loss in other bone resorbing diseases indicates its use as a biomarker for identification of a patient at risk for bone loss in periodontal disease. It is also of interest that the second cytokine, IL-1β, was significantly elevated in our subsequent analysis. IL-1β is a cytokine that can stimulate cells to produce MIP-1α as well as RANK, another important precursor of bone loss.

Only one interproximal area of bone loss was necessary for detection of elevated MIP-1α or IL-1β in saliva. Because evidence of bone loss was absent 6-9 months prior to radiographic evidence and because it was mandated that students be exited from the study as soon as one site with bone loss was detected, it is most likely that these cytokines were derived from a single periodontal pocket site overlying the one tooth that ultimately developed bone loss.

Increasing levels of MIP-1α correlated with increasing pocket depth but not with the number of pockets that developed. Levels of IL-1β also increased in a similar manner. Because periodontal disease is thought to progress from increasing pocket depth to attachment loss to bone loss MIP-1α and IL-1β may be signals of developing disease. While IL-1β was elevated in this study and appears to correlate with levels of MIP-1α, IL-1β is a cytokine that is elevated in both gingival and periodontal inflammation. Thus, presence of IL-1β by itself cannot be viewed as a specific marker of bone loss. Furthermore, IL-1β levels showed only a five-fold difference due to the onset of periodontal disease and thus, IL-1β is not as capable as MIP-1α of discriminating between health and disease.

The approximately 50-fold increase above basal levels of MIP-1α in subjects prior to bone loss indicates that salivary MIP-1α levels can be used as an early indication of bone loss. Moreover, ANCOVA modeling indicated that MIP-1α was the dominant independent variable examined in relation to the number of pockets six mm or greater. Using this statistical modeling method, IL-1β and *A. actinomycetemcomitans* were not as strongly related to the number of pockets.

In conclusion, the longitudinal design used in this study has provided us with data to indicate that salivary levels of the chemokine MIP-1α may be used as a biomarker for identification of a patient in advance of radiographic evidence of bone loss. This evidence is compelling because it is based on samples obtained a minimum of 6-9 months prior to radiographic detection of bone loss in a group of LAP subjects. In conjunction with previous findings, it may be possible to translate this data into a two-step screen for subjects susceptible to bone loss in LAP; the first screen for detection of those who carry *A. actinomycetemcomitans*, and a second screen utilizing MIP-1α to discriminate between the *A. actinomycetemcomitans* carriers who will develop bone loss as opposed to those who remain healthy. Moreover, such a test can pave the way for cost-effective prevention or treatment for underserved children most susceptible to LAP.

We used a sensitive cytokine assay that analyzed 21 cytokines in saliva in a longitudinal study of periodontal disease. Periodontal disease is a progressive disease that results in bone loss over time. In our studies, we took saliva samples every 6 months and found that of the group that developed bone loss only one cytokine was elevated 6 months prior to bone loss. That cytokine was MIP-1α and an extensive review of the literature indicated that MIP-1α was also elevated many months prior to active bone loss in multiple myeloma, a severe cancer that results in massive bone loss throughout the body. Our data and the literature reviewed suggested that MIP-1α is a cytokine that both: 1) attracts monocytes to areas of bone resorption, and 2) then signals these monocytes to become active osteoclasts that cause bone resorption. In our study, we were surprised to find that we could detect elevated levels of MIP-1α in the saliva of patients any where from 6-9 months prior to x-ray evidence of bone loss in these same patients. In addition we have been able to detect both RANKL and Osteoprotegerin in saliva.

Example 2

Following a similar testing procedure as set out in Example 1, tests were run on 16 LAP patients before bone loss was detected, 20 LAP patients after bone loss was detected, 82 healthy patients, and 36 patients with potential disease. Each of these patients had assays run to determine the level of the most likely cytokines present in salivary samples. 40 different cytokines were tested, with MIP-1α, MIP-1β, IL-12 (p40) and IL-1β showing the best results for distinguishing those individuals that would develop bone loss 6-9 months prior to x-ray evidence. As shown in Table 4, there is about a 40 fold elevation in MIP-1α at 6-9 months prior to bone loss, which supports the findings of Example 1. Once again, IL-1β was also one of the cytokines that was elevated, but it was elevated in health, potential disease and after bone loss. According, MIP-1α is preferable as the biomarker for future bone loss due to periodontal disease.

TABLE 4

Relationship of Cytokine Levels in Saliva to Disease Levels

| Cytokine (pg/ml) | Healthy | Potential | LAP before | LAP after |
|---|---|---|---|---|
| MIP-1a | 18.7 (sd = 20.4) | 8.1 (sd = 10.9) | 126.3 (sd = 71.5) | 9.9 (sd = 11.5) |
| MIP-1b | 60.5 (sd = 35.4) | 22 (sd = 24.7) | 89 (sd = 78.6) | 35.4 (sd = 8.9) |
| IL-12(p40) | 48.3 (sd = 57.4) | 14.9 (sd = 34.1) | 82.8 (sd = 117.7) | 18.6 (sd = 58.4) |
| IL-1β | 197.1 (sd = 253.6) | 134.5 (sd = 191.8) | 392 (sd = 286.3) | 147.5 (sd = 127.5) |

Further, we have also done a small study that examined individuals who were undergoing tooth movement where bone loss is generated by force as opposed to infection, as in the case of periodontal disease. In this study, both saliva and crevicular fluid was collected and assayed for the presence and level of the markers seen in periodontal disease. Whereas in the case of periodontal bone loss a 40-fold elevation in the biomarker MIP-1α was seen in the diseased subjects, in this study, no difference was seen in patients undergoing severe tooth movement as compared to controls with respect to levels of MIP-1α. These findings indicate that MIP-1α as biomarker of bone loss in the case of periodontal disease will not be confused with bone loss resulting from physical trauma (i.e. tooth movement). Thus, traumatic bone loss measures will not conflict with bone loss resulting from inflammatory response to infection.

These findings further indicate that the mechanisms for bone loss are different as reflected in the bone markers seen in the crevicular fluid and in the saliva. Thus, use of MIP-1α as a salivary and periodontal pocket fluid test to predict radiographic evidence of bone loss in periodontal disease will not be confused with bone loss resulting from orthodontic tooth movement or other traumatic stressors.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

The invention claimed is:

1. A method of locating periodontal disease within a patient's mouth comprising: depositing selected adsorptive articles into respective periodontal pocket sites for a selected period of time to obtain samples of fluid from said periodontal pocket sites; individually retrieving the adsorptive articles from the respective periodontal pocket sites and placing the adsorptive articles into respective test containers corresponding to the respective periodontal pocket sites; contacting the fluid samples individually with reagent to measure the level of MIP-1α, and locating periodontal pocket having MIP-1α level greater than 40 pg/ml.

2. The method of claim 1, wherein the level of MIP-1α is greater than about 200 pg/ml.

3. The method of claim 2, wherein the level is from about 200 pg/ml to 2000 pg/ml.

4. The method of claim 2, wherein the level is from about 500 pg/ml to about 1,500 pg/ml.

5. The method of claim 2, wherein the level is from about 750 pg/ml to about 1,250 pg/ml.

6. The method of claim 1, wherein the biomarker is identified prior to radiographic evidence of bone loss.

7. The method of claim 1, wherein the selected adsorptive articles are selected from the group consisting of beads of hydroxyapatite, sterile endodontic paper points, micropipettes, and capillary tubes.

8. The method of claim 1, wherein the step, analyzing the fluid samples individually to identify the presence of a biomarker at a level that indicates periodontal disease, comprises using multiplexed sandwich immunoassays.

* * * * *